United States Patent
Mohapatra et al.

(10) Patent No.: US 11,951,152 B1
(45) Date of Patent: Apr. 9, 2024

(54) MICROPARTICLE COMPOSITIONS FOR CONTROLLED DELIVERY OF TELMISARTAN AND ACTINOMYCIN D

(71) Applicant: University of South Florida, Tampa, FL (US)

(72) Inventors: Subhra Mohapatra, Lutz, FL (US); Shyam S. Mohapatra, Lutz, FL (US); Eleni Markoutsa, Tampa, FL (US); Alejandro J. Gonzalez, Brandon, FL (US); Heta N. Jadhav, Tampa, FL (US)

(73) Assignees: University of South Florida, Tampa, FL (US); THE UNITED STATES GOVERNMENT AS REPRESENTED BY THE DEPARTMENT OF VETERAN AFFAIRS, Washington, DC (US)

( * ) Notice: Subject to any disclaimer, the term of this patent is extended or adjusted under 35 U.S.C. 154(b) by 587 days.

(21) Appl. No.: 17/025,277

(22) Filed: Sep. 18, 2020

Related U.S. Application Data

(60) Provisional application No. 62/902,149, filed on Sep. 18, 2019.

(51) Int. Cl.
| | |
|---|---|
| A61K 38/12 | (2006.01) |
| A61K 9/127 | (2006.01) |
| A61K 9/16 | (2006.01) |
| A61K 31/4184 | (2006.01) |
| A61K 31/704 | (2006.01) |
| A61K 47/08 | (2006.01) |
| A61K 47/24 | (2006.01) |
| A61P 35/00 | (2006.01) |

(52) U.S. Cl.
CPC .............. *A61K 38/12* (2013.01); *A61K 9/127* (2013.01); *A61K 9/1652* (2013.01); *A61K 31/4184* (2013.01); *A61K 31/704* (2013.01); *A61K 47/08* (2013.01); *A61K 47/24* (2013.01); *A61P 35/00* (2018.01)

(58) Field of Classification Search
CPC ...... A61K 38/12; A61K 47/08; A61K 9/1127; A61P 35/00
See application file for complete search history.

(56) References Cited

FOREIGN PATENT DOCUMENTS

CN 103962075 B 1/2016

OTHER PUBLICATIONS

Begona Seijo et al. Microspheres containing lipid/chitosan nanoparticles complexes for pulmonary delivery of therapeutic proteins, Eur. J of Pharmaceutics and Biopharmaceutics, 69, 83-93. (Year: 2008).*
Demetrios Papahadjopoulos et al. Use of Lipid Vesicles as Carriers to Introduce Actinomycin D into Resistant Tumor cells, Cancer Research, 36, 2988-2994. (Year: 1976).*
Li Liu et al. Monodisperse core-shell chitosan microcapsules for pH-responsive burst release of hydrophobic drugs, Soft Matter,7, 4821-4827 (Year: 2011).*
Upsanan Yadav et al. Formulation of Nanoparticles of Telmisartan incorporated in carboxymethyl chitosan for the better drug delivery and enhanced bioavailability, Asian J of Pharmaceutical and Clinical Research, 10(9), 236-241. (Year: 2017).*
Liu et al.; "Monodisperse core-shell chitosan microcapsules for pH-responsive burst release of hydrophobic drugs"; Soft Matter, 2011, 7, 4821; Nov. 30, 2020; 7 pages.
Jonassen et al.; "Stability of Chitosan Nanoparticles Cross-Linked with Tripolyphosphate"; Biomacromolecules 2012, 13, 3747-3756; Oct. 9, 2012; 10 pages.
Meenach et al.; "Design, physicochemical characterization, and optimization of organic solution advanced spray-dried inhalable dipalmitoylphosphatidylcholine (DPPC) and dipalmitoylphosphatidylethanolamine poly(ethylene glycol) (DPPE-PEG) microparticles and nanoparticles for targeted respiratory nanomedicine delivery as dry powder inhalation aerosols"; International Journal of Nanomedicine; dated Jan. 15, 2013; 19 pages.
Yang et al.; "Core-Shell Chitosan Microcapsules for Programmed Sequential Drug Release"; ACS Appl. Mater. Interfaces 2016, 8, 10524-10534; Dated Apr. 7, 2016; 11 pages.
Manchanda et al.; "Topical delivery of acetazolamide by encapsulating in mucoadhesive nanoparticles"; Asian Journal of Pharmaceutical Sciences 12 (2017) 550-557; 8 pages.
Du et al.; "The design of pH-sensitive chitosan-based formulations for gastrointestinal delivery"; Drug Discov Today (2015), Mar. 2015; 8 pages.
Yadav et al; "Formulation of Nanoparticles of Telmisartan Incorporated in Carboxymethyl Chitosan for the Better Drug Delivery and Enhanced Bioavailability"; Asian J Pharm Clin Res, vol. 10, Issue 9, 2017, 236-241; May 29, 2017; 6 pages.
Biscarat et al.; "Effect of chemical cross-linking on gelatin membrane solubility with anon-toxic and non-volatile agent: Terephthalaldehyde"; International Journal of Biological Macromolecules 74 (2015) 5-11; Jul. 16, 2014; 7 pages.
Sharma et al.; "Crosslinked chitosan nanoparticle formulations for delivery from pressurized metered dose inhalers"; European Journal of Pharmaceutics and Biopharmaceutics 81 (2012) 74-81; Aug. 15, 2011; 8 pages.

* cited by examiner

*Primary Examiner* — Michael G. Hartley
*Assistant Examiner* — Jagadishwar R Samala
(74) *Attorney, Agent, or Firm* — Meunier Carlin & Curfman LLC

(57) ABSTRACT

This disclosure is directed to therapeutic compositions, and more particularly to microparticle compositions for the controlled delivery of telmisartan and actinomycin D.

18 Claims, 6 Drawing Sheets

MICROPARTICLE COMPOSITIONS FOR CONTROLLED DELIVERY OF TELMISARTAN AND ACTINOMYCIN D

CROSS-REFERENCE TO RELATED APPLICATIONS

This application claims the benefit of priority to U.S. Provisional Application No. 62/902,149, filed Sep. 18, 2019, the disclosure of which is incorporated herein by reference in its entirety.

STATEMENT REGARDING FEDERALLY SPONSORED RESEARCH OR DEVELOPMENT

This invention was made with government support under Grant No. BX003413 awarded by the US Department of Veterans Affairs. The Government has certain rights in the invention.

TECHNICAL FIELD

This disclosure relates to therapeutic compositions, and more particularly to microparticle compositions for the controlled delivery of telmisartan and actinomycin D.

BACKGROUND

Lung cancer remains the deadliest cancer of any type, with cases reported in 1.8 million people and 1.6 deaths occurring worldwide in 2012. Despite the myriad of treatment options available, the five-year survival rate in the United States is just 19.4%, with the low survival rate being primarily due to the development of drug resistance in metastatic tumors. There is a clear need for the development of new treatments of lung cancer, as well as other cancers. This disclosure addresses this as well as other needs.

SUMMARY

The present disclosure provides therapeutic compositions that allow for differential, controlled release of telmisartan and actinomycin D that may be used in the treatment of cancer. The therapeutic composition comprises liposomal microparticles which encapsulate at least two different types of crosslinked chitosan nanoparticles that are separately loaded with telmisartan and actinomycin D. These compositions allow for rapid release of actinomycin D upon exposure of the composition to an acidic environment (such as a tumor environment) while allowing for a sustained release of telmisartan.

Thus, in one aspect, a therapeutic composition is provided comprising:

- a plurality of liposomal microparticles;
- a plurality of terephthalaldehyde (TPA)-crosslinked chitosan nanoparticles encapsulated within the liposomal microparticles, wherein the TPA-crosslinked chitosan nanoparticles are loaded with actinomycin D; and
- a plurality of tripolyphosphate (TPP)-crosslinked chitosan nanoparticles encapsulated within the liposomal microparticles, wherein the TPP-crosslinked chitosan nanoparticles are loaded with telmisartan.

In some embodiments, the liposomal microparticles have an average particle diameter ranging from about 25 to about 55 microns. In some embodiments, the liposomal microparticles comprise dipalmitoylphosphatidylcholine (DPPC).

In some embodiments, the TPA-crosslinked chitosan nanoparticles have an average particle diameter ranging from about 300 nm to about 700 nm at a pH of greater than about 7. In some embodiments, the TPA-crosslinked chitosan nanoparticles have a zeta potential ranging from about 2 mV to about 5 mV at a pH of greater than about 7. In some embodiments, the TPA-crosslinked chitosan nanoparticles release telmisartan at a pH of less than about 7. In some embodiments, the average particle diameter of the TPA-crosslinked chitosan nanoparticles increases by an amount ranging from about 100 nm to about 300 nm at a pH of less than about 7. In some embodiments, the zeta potential of the TPA-crosslinked chitosan nanoparticles increases by an amount ranging from about 5 mV to about 15 mV at a pH of less than about 7. In some embodiments, the TPA-crosslinked chitosan nanoparticles release at least 25% of the loaded actinomycin D within 30 minutes at a pH of less than about 7. In some embodiments, acetazolamide is conjugated to the surface of the TPA-crosslinked chitosan nanoparticles.

In some embodiments, the TPP-crosslinked chitosan nanoparticles have an average particle diameter from about 50 nm to about 500 nm. In some embodiments, the TPP-crosslinked chitosan nanoparticles have a zeta potential ranging from about 5 mV to about 50 mV. In some embodiments, the TPP-crosslinked chitosan nanoparticles provide sustained release of telmisartan. In some embodiments, acetazolamide is conjugated to the surface of the TPP-crosslinked chitosan nanoparticles.

In some embodiments, the therapeutic compositions further comprise one or more additional therapeutic agents. In some embodiments, the therapeutic compositions are formulated for delivery to the lung.

In another aspect, a method of treating cancer in a subject is provided comprising administering a therapeutically effective amount of the composition described herein to the subject. In some embodiments, the cancer is lung cancer. In some embodiments, the composition is administered to the lung.

The details of one or more embodiments of the disclosure are set forth in the accompanying drawings and the description below. Other features, objects, and advantages of the disclosure will be apparent from the description and drawings, and from the claims.

DESCRIPTION OF DRAWINGS

FIG. 1A is a schematic representation of the therapeutic compositions described herein. FIG. 1B are transmission electron microscopy and fluorescence microscopy images of a representative microparticle composition as described herein.

FIGS. 2A-2E show the development of a lung-targeted liposomal microparticle platform. The microparticles were prepared with DiR using dipalmitoylphosphatidylcholine (DPPC) lipid in $CHCl_3$:MeOH at a 2:1 ratio. FIG. 2A shows a dynamic laser scattering image of the microparticles. FIGS. 2B and 2C show IVIS imaging of mice injected intravenously with the liposomal microparticles. FIGS. 2D and 2E are photomicrographs of the liposomal microparticles in the deep lung (FIG. 2D) and collaged lung (FIG. 2E).

FIG. 3A shows the effect of pH on TPA-crosslinked nanoparticle size via dynamic laser scattering data (upper) and TEM images (lower). FIGS. 3B and 3C show differential drug release from the chitosan nanoparticles encapsulating FITC-dextran (FIG. 3B) or Nile Red (FIG. 3C). FIG.

3D shows the fluorescence confocal microscopy images of A549 cells treated with TPA-versus TPP-crosslinked Nile Red-labeled nanoparticles for 90 minutes. The lysosomes were stained with Lyso tracker green DND-26. Pearson Corr Coeff was estimated using Imagej-Fiji.

Figure 4A:
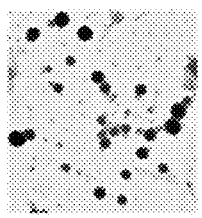
Figure 4B:
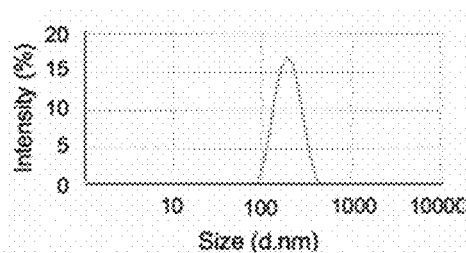
Figure 4C:
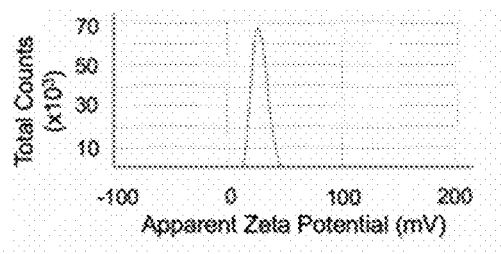
Figure 4D:
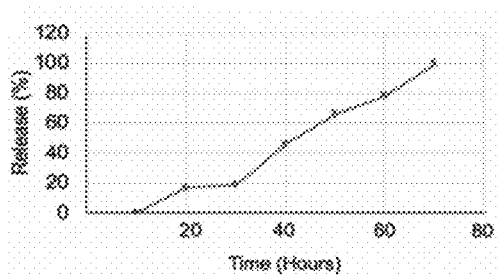
Figure 4E:
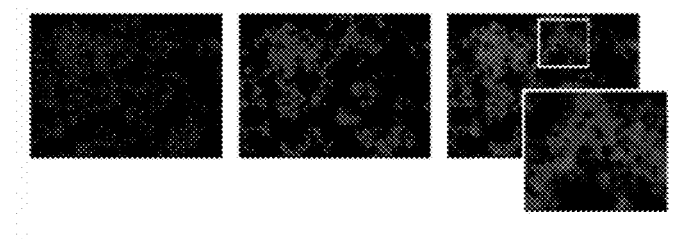

FIGS. 4A-4E show data related to the TPP-crosslinked chitosan nanoparticles described herein. FIG. 4A show TEM images of the TPP-crosslinked nanoparticles. FIG. 4B shows the size distribution of the particles as determined by DLS. FIG. 4C shows the zeta potential of the nanoparticles. FID. 4D shows the drug release from the nanoparticles in PBS at 37 degrees Celsius. FIG. 4E shows the uptake of Cy3-labeled nanoparticles by LLC cells (24 hours).

Like reference symbols in the various drawings indicate like elements.

DETAILED DESCRIPTION

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As can be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It can be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of.

As used in the specification and the appended claims, the singular forms "a," "an" and "the" include plural referents unless the context clearly dictates otherwise. Thus, for example, reference to "a liposomal microparticle", "a chitosan nanoparticle", or "a therapeutic agent", includes, but is not limited to, two or more such liposomal microparticles, chitosan nanoparticles, or therapeutic agents, and the like.

It should be noted that ratios, concentrations, amounts, and other numerical data can be expressed herein in a range format. It can be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it can be understood that the particular value forms a further aspect. For example, if the value "about 10" is disclosed, then "10" is also disclosed.

When a range is expressed, a further aspect includes from the one particular value and/or to the other particular value. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the term "effective amount" refers to an amount that is sufficient to achieve the desired modification of a physical property of the composition or material. For example, an "effective amount" of a monomer refers to an amount that is sufficient to achieve the desired improvement in the property modulated by the formulation component, e.g. desired antioxidant release rate or viscoelasticity. The specific level in terms of wt % in a composition required as an effective amount will depend upon a variety of factors including the amount and type of monomer, amount and type of polymer, e.g., acrylamide, amount of antioxidant, and desired release kinetics.

As used herein, the term "therapeutically effective amount" refers to an amount that is sufficient to achieve the desired therapeutic result or to have an effect on undesired symptoms but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors within the knowledge and expertise of the health practitioner and which may be well known in the medical arts. In the case of treating a particular disease or condition, in some instances, the desired response can be inhibiting the progression of the disease or condition. This may involve only slowing the progression of the disease temporarily. However, in other instances, it may be desirable to halt the progression of the disease permanently. This can be monitored by routine diagnostic methods known to one of ordinary skill in the art for any particular disease. The desired response to treatment of the disease or condition also can be delaying the onset or even preventing the onset of the disease or condition.

For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. It is generally preferred that a maximum dose of the pharmacological agents of the invention (alone or in combination with other therapeutic agents) be used, that is, the highest safe dose according to sound medical judgment. It will be understood by those of ordinary skill in the art however, that a patient may insist upon a lower dose or tolerable dose for medical reasons, psychological reasons or for virtually any other reasons.

A response to a therapeutically effective dose of a disclosed drug delivery composition can be measured by determining the physiological effects of the treatment or medication, such as the decrease or lack of disease symptoms following administration of the treatment or pharmacological agent. Other assays will be known to one of ordinary skill in the art and can be employed for measuring the level of the response. The amount of a treatment may be varied for example by increasing or decreasing the amount of a disclosed compound and/or pharmaceutical composition, by changing the disclosed compound and/or pharmaceutical composition administered, by changing the route of administration, by changing the dosage timing and so on. Dosage can vary, and can be administered in one or more dose administrations daily, for one or several days. Guidance can be found in the literature for appropriate dosages for given classes of pharmaceutical products.

As used herein, the term "prophylactically effective amount" refers to an amount effective for preventing onset or initiation of a disease or condition.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed. As used herein, the terms "optional" or "optionally" means that the subsequently described event or circumstance can or cannot occur, and that the description includes instances where said event or circumstance occurs and instances where it does not.

As used interchangeably herein, "subject," "individual," or "patient" can refer to a vertebrate organism, such as a mammal (e.g. human). "Subject" can also refer to a cell, a population of cells, a tissue, an organ, or an organism, preferably to human and constituents thereof.

As used herein, the terms "treating" and "treatment" can refer generally to obtaining a desired pharmacological and/or physiological effect. The effect can be, but does not necessarily have to be, prophylactic in terms of preventing or partially preventing a disease, symptom or condition thereof, such as an ophthalmological disorder. The effect can be therapeutic in terms of a partial or complete cure of a disease, condition, symptom or adverse effect attributed to the disease, disorder, or condition. The term "treatment" as used herein can include any treatment of ophthalmological disorder in a subject, particularly a human and can include any one or more of the following: (a) preventing the disease from occurring in a subject which may be predisposed to the disease but has not yet been diagnosed as having it; (b) inhibiting the disease, i.e., arresting its development; and (c) relieving the disease, i.e., mitigating or ameliorating the disease and/or its symptoms or conditions. The term "treatment" as used herein can refer to both therapeutic treatment alone, prophylactic treatment alone, or both therapeutic and prophylactic treatment. Those in need of treatment (subjects in need thereof) can include those already with the disorder and/or those in which the disorder is to be prevented. As used herein, the term "treating", can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, e.g., such as treating the pain of a subject by administration of an analgesic agent even though such agent does not treat the cause of the pain.

As used herein, "dose," "unit dose," or "dosage" can refer to physically discrete units suitable for use in a subject, each unit containing a predetermined quantity of a disclosed compound and/or a pharmaceutical composition thereof calculated to produce the desired response or responses in association with its administration.

As used herein, "therapeutic" can refer to treating, healing, and/or ameliorating a disease, disorder, condition, or side effect, or to decreasing in the rate of advancement of a disease, disorder, condition, or side effect.

Therapeutic Compositions

The present disclosure provides therapeutic compositions comprising liposomal microparticles which encapsulate both terephthalaldehyde (TPA)-crosslinked and tripolyphosphate (TPP)-crosslinked chitosan nanoparticles. The TPA-crosslinked chitosan nanoparticles are loaded with actinomycin D and allow rapid release of the drug in a pH dependent manner. The TPP-crosslinked chitosan nanoparticles are instead loaded with telmisartan and release the drug in a sustained fashion that is not dependent upon pH.

Thus in one aspect, a therapeutic composition is provided comprising:
  a plurality of liposomal microparticles;
  a plurality of terephthalaldehyde (TPA)-crosslinked chitosan nanoparticles encapsulated within the liposomal microparticles, wherein the TPA-crosslinked chitosan nanoparticles are loaded with actinomycin D; and a plurality of tripolyphosphate (TPP)-crosslinked chitosan nanoparticles encapsulated within the liposomal microparticles, wherein the TPP-crosslinked chitosan nanoparticles are loaded with telmisartan.

The liposomal microparticles may comprise one or lipids selected from the group consisting of fatty acids, lysolipids, sphingolipids, sphingomyelin, glycolipids, glucolipids, glycosphingolipids, palmitic acid, stearic acid, arachidonic acid, oleic acid, lipids bearing sulfonated mono-, di-, oligo- or polysaccharides, lipids with ether and ester-linked fatty acids, polymerized lipids, diacetyl phosphate, stearyl amine, cardiolipin, phospholipids, synthetic phospholipids with asymmetric acyl chains, and lipids bearing a covalently bound polymer. In some embodiments, the liposomal microparticles may comprise a phospholipid selected from the group consisting of phosphatidylcholines, lysophosphatidylcholines, phosphatidylethanolamines, phosphatidylinositols, phosphatidylglycerols, phosphatidic acid, phosphatidylserines, and mixtures thereof. In some embodiments, the liposomal microparticles may comprise a phospholipid in an admixture with a modifying agent selected from the group consisting of cholesterols, stearyl amines, stearic acid, tocopherols, and mixtures thereof. In some embodiments, the liposomal microparticles may comprise a phosphatidylcholine selected from the group consisting of dioleoylphosphatidylcholine (DOPC), dilauroylphosphatidylcholine (DLPC), dimyristoylphosphatidylcholine (DMPC), dipalmitoylphosphatidylcholine (DPPC), distearoylphosphatidylcholine (DSPC), and mixtures thereof. In particular embodiments, the liposomal microparticles comprise DPPC.

In some embodiments, the liposomal microparticles may have an average particle diameter ranging from about 25 microns to about 55 microns, for example from about 30 microns to about 55 microns, from about 35 microns to about 55 microns, from about 40 microns to about 55 microns, from about 45 microns to about 55 microns, from about 50 microns to about 55 microns, from about 25 microns to about 50 microns, from about 30 microns to about 50 microns, from about 35 microns to about 50 microns, from about 40 microns to about 50 microns, from about 45 microns to about 50 microns, from about 25 microns to about 45 microns, from about 30 microns to about 45 microns, from about 35 microns to about 45 microns, from about 40 microns to about 45 microns, from about 25 microns to about 40 microns, from about 30 microns to about 40 microns, from about 35 microns to about 40 microns, from about 25 microns to about 35 microns, from about 30 microns to about 35 microns, or from about 25 microns to about 30 microns. In some embodiments, the liposomal microparticles may have an average particle diameter of about 25 microns, about 27 microns, about 30 microns, about 33 microns, about 35 microns, about 37 microns, about 40 microns, about 43 microns, about 45 microns, about 47 microns, about 50 microns, about 53 microns, or about 55 microns.

In another aspect, the therapeutic compositions described herein comprise terephthalaldehyde (TPA)-crosslinked chitosan nanoparticles. TPA-crosslinked nanoparticles provide release of therapeutics loaded therein in a pH-dependent manner due to the cross-linking being due to the formation of Schiff bases between TPA and the amino groups of the chitosan nanoparticles. Upon exposure to an environment having a pH of less than about 7, the Schiff base crosslinks are hydrolyzed, allowing rapid release of any therapeutic components contained therein.

In some embodiments, the TPA-crosslinked chitosan nanoparticles have an average particle diameter ranging from about 300 nm to about 700 nm at a pH of greater than about 7. In some embodiments, the TPA-crosslinked chitosan nanoparticles have an average particle diameter at a pH of greater than about 7 ranging from about 300 nm to about 700 nm, from about 350 nm to about 700 nm, from about 400 nm to about 700 nm, from about 450 nm to about 700 nm, from about 500 nm to about 700 nm, from about 550 nm to about 700 nm, from about 600 nm to about 700 nm, from about 650 nm to about 700 nm, from about 300 nm to about 650 nm, from about 350 nm to about 650 nm, from about 400 nm to about 650 nm, from about 450 nm to about 650 nm, from about 500 nm to about 650 nm, from about 550 nm to about 650 nm, from about 600 nm to about 650 nm, from about 300 nm to about 600 nm, from about 350 nm to about 600 nm, from about 400 nm to about 600 nm, from about 450 nm to about 600 nm, from about 500 nm to about 600 nm, from about 550 nm to about 600 nm, from about 300 nm to about 550 nm, from about 350 nm to about 550 nm, from about 400 nm to about 550 nm, from about 450 nm to about 550 nm, from about 500 nm to about 550 nm, from about 300 nm to about 500 nm, from about 350 nm to about 500 nm, from about 400 nm to about 500 nm, from about 450 nm to about 500 nm, from about 300 nm to about 450 nm, from about 350 nm to about 450 nm, from about 400 nm to about 450 nm, from about 300 nm to about 400 nm, from about 350 nm to about 400 nm, or from about 300 nm to about 350 nm. In some embodiments, the TPA-crosslinked chitosan nanoparticles have an average particle diameter at a pH of greater than about 7 of about 300 nm, about 325 nm, about 350 nm, about 375 nm, about 400 nm, about 425 nm, about 450 nm, about 475 nm, about 500 nm, about 525 nm, about 550 nm, about 575 nm, about 600 nm, about 625 nm, about 650 nm, about 675 nm, or about 700 nm.

In some embodiments, the TPA-crosslinked chitosan nanoparticles have a zeta potential ranging from about 2 mV to about 5 mV at a pH of greater than about 7. In some embodiments, the TPA-crosslinked chitosan nanoparticles have a zeta potential at a pH of greater than about 7 ranging from about 2 mV to about 5 mV, about 2.5 mV to about 5 mV, about 3 mV to about 5 mV, about 3.5 mV to about 5 mV, about 4 mV to about 5 mV, about 4.5 mV to about 5 mV, from about 2 mV to about 4.5 mV, about 2.5 mV to about 4.5 mV, about 3 mV to about 4.5 mV, about 3.5 mV to about 4.5 mV, about 4 mV to about 4.5 mV, from about 2 mV to about 4 mV, about 2.5 mV to about 4 mV, about 3 mV to about 4 mV, about 3.5 mV to about 4 mV, from about 2 mV to about 3.5 mV, about 2.5 mV to about 2.5 mV, about 3 mV to about 2.5 mV, from about 2 mV to about 3 mV, from about 2.5 mV to about 3 mV, and from about 2 mV to about 2.5 mV. In some embodiments, the TPA-crosslinked chitosan nanoparticles have a zeta potential at a pH of greater than about 7 of about 2 mV, about 2.2 mV, about 2.4 mV, about 2.6 mV, about 2.8 mV, about 3 mV, about 3.2 mV, about 3.4 mV, about 3.6 mV, about 3.8 mV, about 4 mV, about 4.2 mV, about 4.4 mV, about 4.6 mV, about 4.8 mV, or about 5 mV.

In another aspect, the TPA-crosslinked chitosan nanoparticles are loaded with actinomycin D. Actinomycin D (also known as Dactinomycin) is a small molecule chemotherapeutic having the chemical structure:

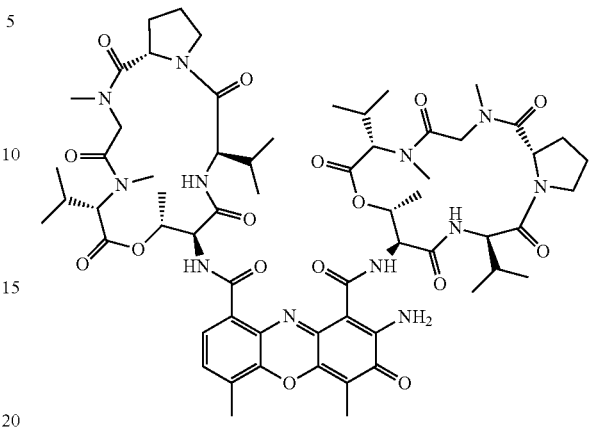

Actinomycin D has been previously used as an antibiotic or to treat cancer and may work by inhibiting or preventing transcription and the creation of RNA. While not wishing to be bound by any one theory, actinomycin D may bind DNA at the transcription initiation complex and prevent elongation of the RNA chain by RNA polymerases. Actinomycin D may bind to DNA and block the progress of RNA polymerases during transcription. Actinomycin D may also inhibit topoisomerases, causing strain on the DNA molecule and leading to double stranded breaks. Further, actinomycin D may also interfere with DNA replication.

When exposed to an environment having a pH of less than about 7 (for example, a pH of about 6, about 5, about 4, or about 3), the Schiff bases formed by the TPA-crosslinks in the TPA-crosslinked chitosan nanoparticles are hydrolyzed, leading to rapid release of the actinomycin D loaded therein. This rapid release is facilitated both by removal of physical impediments imposed by the TPA-crosslinking as well as an overall increase in the size and zeta potential of the chitosan nanoparticles. In some embodiments, the average particle diameter of the TPA-crosslinked chitosan nanoparticles increases by an amount ranging from about 100 nm to about 300 nm (for example, by about 100 nm, 150 nm, 200 nm, 250 nm, or 300 nm) at a pH of less than about 7. In some embodiments, the zeta potential of the TPA-crosslinked chitosan nanoparticles increases by an amount ranging from about 5 mV to about 15 mV (for example, by about 5 mV, 6 mV, 7 mV, 8 mV, 9 mV, 10 mV, 11 mV, 12 mV, 13 mV, 14 mV, or 15 mV) at a pH of less than about 7.

In some embodiments, the TPA-crosslinked chitosan nanoparticles release at least about 25% of the loaded actinomycin D within 30 minutes at a pH of less than about 7. In some embodiments, the TPA-crosslinked chitosan nanoparticles release at least about 25%, about 30%, about 35%, about 40%, about 45%, about 50%, about 55%, about 60%, about 65%, about 70%, about 75% or more of the loaded actinomycin D within 30 minutes at a pH of less than about 7.

In another aspect, the therapeutic compositions described herein comprise tripolyphosphate (TPP)-crosslinked chitosan nanoparticles. Compared to the TPA-crosslinked chitosan nanoparticles described above, the TPP-crosslinked chitosan particles are stable over a variety of pH conditions, leading instead to a sustained release of any therapeutic components (such as telmisartan) loaded therein. As used herein, "sustained release" refers to release rate of a loaded therapeutic substance (such as telmisartan) which has an initial release percentage (i.e., the release percentage up to one day after administration) preferably not more than about 50%, for example from about 1% to about 30%, 2% to about 20%, or 2% to about 15%, and where a constant amount of the loaded therapeutic substance is release over a long period of time.

In some embodiments, the TPP-crosslinked chitosan nanoparticles have an average particle diameter from about 50 nm to about 500 nm. In some embodiments, the TPP-crosslinked chitosan nanoparticles have an average particle diameter ranging from about 50 nm to about 500 nm, from about 100 nm to about 500 nm, from about 150 nm to about 500 nm, from about 200 nm to about 500 nm, from about 250 nm to about 500 nm, from about 300 nm to about 500 nm, from about 350 nm to about 500 nm, from about 400 nm to about 500 nm, from about 450 nm to about 500 nm, from about 50 nm to about 450 nm, from about 100 nm to about 450 nm, from about 150 nm to about 450 nm, from about 200 nm to about 450 nm, from about 250 nm to about 450 nm, from about 300 nm to about 450 nm, from about 350 nm to about 450 nm, from about 400 nm to about 450 nm, from about 50 nm to about 400 nm, from about 100 nm to about 400 nm, from about 150 nm to about 400 nm, from about 200 nm to about 400 nm, from about 250 nm to about 400 nm, from about 300 nm to about 400 nm, from about 350 nm to about 400 nm, from about 50 nm to about 350 nm, from about 100 nm to about 350 nm, from about 150 nm to about 350 nm, from about 200 nm to about 350 nm, from about 250 nm to about 350 nm, from about 300 nm to about 350 nm, from about 50 nm to about 300 nm, from about 100 nm to about 300 nm, from about 150 nm to about 300 nm, from about 200 nm to about 300 nm, from about 250 nm to about 300 nm, from about 50 nm to about 250 nm, from about 100 nm to about 250 nm, from about 150 nm to about 250 nm, from about 200 nm to about 250 nm, from about 50 nm to about 200 nm, from about 100 nm to about 200 nm, from about 150 nm to about 200 nm, from about 50 nm to about 150 nm, from about 100 nm to about 150 nm, or from about 50 nm to about 100 nm.

In some embodiments, the TPP-crosslinked chitosan nanoparticles have a zeta potential ranging from about 5 mV to about 50 mV. In some embodiments, the TPP-crosslinked chitosan nanoparticles have a zeta potential ranging from about 5 mV to about 50 mV, from about 10 mV to about 50 mV, from about 15 mV to about 50 mV, from about 20 mV to about 50 mV, from about 25 mV to about 50 mV, from about 30 mV to about 50 mV, from about 35 mV to about 50 mV, from about 40 mV to about 50 mV, from about 45 mV to about 50 mV, from about 5 mV to about 45 mV, from about 10 mV to about 45 mV, from about 15 mV to about 45 mV, from about 20 mV to about 45 mV, from about 25 mV to about 45 mV, from about 30 mV to about 45 mV, from about 35 mV to about 45 mV, from about 40 mV to about 45 mV, from about 5 mV to about 40 mV, from about 10 mV to about 40 mV, from about 15 mV to about 40 mV, from about 20 mV to about 40 mV, from about 25 mV to about 40 mV, from about 30 mV to about 40 mV, from about 35 mV to about 40 mV, from about 5 mV to about 35 mV, from about 10 mV to about 35 mV, from about 15 mV to about 35 mV, from about 20 mV to about 35 mV, from about 25 mV to about 35 mV, from about 30 mV to about 35 mV, from about 5 mV to about 30 mV, from about 10 mV to about 30 mV, from about 15 mV to about 30 mV, from about 20 mV to about 30 mV, from about 25 mV to about 30 mV, from about 5 mV to about 25 mV, from about 10 mV to about 25 mV, from about 15 mV to about 25 mV, from about 20 mV to about 25 mV, from about 5 mV to about 20 mV, from about 10 mV to about 20 mV, from about 15 mV to about 20 mV, from about 5 mV to about 15 mV, from about 10 mV to about 15 mV, or from about 5 mV to about 10 mV.

In another aspect, the TPP-crosslinked chitosan nanoparticles are loaded with telmisartan. Telmisartan is an angiotensin II receptor antagonist (angiotensin receptor blocker, ARB) having the chemical structure:

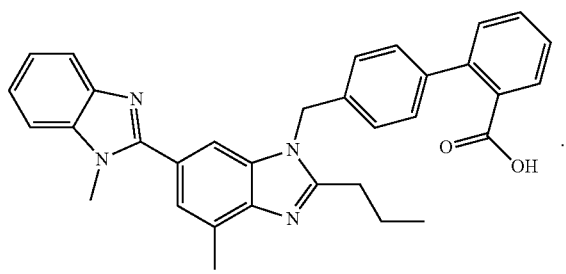 [SMILES: CCCc1nc2c(C)cc(-c3nc4ccccc4n3C)cc2n1Cc1ccc(-c2ccccc2C(=O)O)cc1]

Telmisartan binds to the angiotensin II receptor type 1 ($AT_1$) with a binding affinity about 3000 times greater for $AT_1$ than for $AT_2$. Telmisartan has been previously used in the management of hypertension. Telmisartan may modulate peroxisome proliferator-activated receptor gamma (PPAR-γ), a central regulator of insulin and glucose metabolism. While not wishing to be bound to one theory, telmisartan may increase drug permeability in tumors by increasing the penetration via reduction in collagen production.

In some embodiments, acetazolamide may be conjugated onto the surface of the TPA-crosslinked chitosan nanoparticles, the TPP-crosslinked chitosan nanoparticles, or both. Acetazolamide is a carbonic anhydrase inhibitor having the chemical structure:

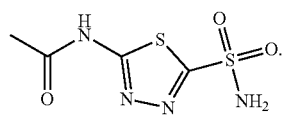

Conjugated acetazolamide is used as a hypoxia targeting moiety in the therapeutic compositions described herein, as tumor cells undergoing hypoxia are noted to show increased expression of carbonic anhydrases.

In some embodiments, the therapeutic compositions described herein may further comprise one or more additional therapeutic agents, for example an anti-cancer agent such as an antimetabolite, an antimitotic agent, a chemotherapeutic agent, a biologic, and the like.

Methods of Treatment

Methods of treating a clinical condition by administration of a disclosed drug delivery composition are also provided herein. A clinical condition can be a clinical disorder, disease, dysfunction or other condition that can be ameliorated by a therapeutic composition. In one aspect, the present disclosure provides methods for treating cancer in a subject in need thereof, wherein the method comprises administering a therapeutically effective amount of a therapeutic composition described herein.

The term "neoplasia" or "cancer" is used throughout this disclosure to refer to the pathological process that results in the formation and growth of a cancerous or malignant neoplasm, i.e., abnormal tissue (solid) or cells (non-solid) that grow by cellular proliferation, often more rapidly than normal and continues to grow after the stimuli that initiated the new growth cease. Malignant neoplasms show partial or complete lack of structural organization and functional coordination with the normal tissue and most invade surrounding tissues, can metastasize to several sites, are likely to recur after attempted removal and may cause the death of the patient unless adequately treated. As used herein, the term neoplasia is used to describe all cancerous disease states and embraces or encompasses the pathological process associated with malignant, hematogenous, ascitic and solid tumors. The cancers which may be treated by the compositions disclosed herein may comprise carcinomas, sarcomas, lymphomas, leukemias, germ cell tumors, or blastomas.

Carcinomas which may be treated by the compositions of the present disclosure include, but are not limited to, acinar carcinoma, acinous carcinoma, alveolar adenocarcinoma, carcinoma adenomatosum, adenocarcinoma, carcinoma of adrenal cortex, alveolar carcinoma, alveolar cell carcinoma, basal cell carcinoma, carcinoma basocellular, basaloid carcinoma, basosquamous cell carcinoma, breast carcinoma, bronchioalveolar carcinoma, bronchiolar carcinoma, cerebriform carcinoma, cholangiocellular carcinoma, chorionic carcinoma, colloid carcinoma, comedocarcinoma, corpus carcinoma, cribriform carcinoma, carcinoma en cuirasse, carcinoma *cutaneum*, cylindrical carcinoma, cylindrical cell carcinoma, duct carcinoma, carcinoma durum, embryonal carcinoma, encephaloid carcinoma, epibulbar carcinoma, epidermoid carcinoma, carcinoma epitheliate adenoids, carcinoma exulcere, carcinoma fibrosum, gelatinform carcinoma, gelatinous carcinoma, giant cell carcinoma, gigantocellulare, glandular carcinoma, granulose cell carcinoma, hair matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, lentivular carcinoma, carcinoma lenticulare, lipomatous carcinoma, lymphoepithelial carcinoma, carcinoma mastotoids, carcinoma medullare, medullary carcinoma, carcinoma melanodes, melanotonic carcinoma, mucinous carcinoma, carcinoma muciparum, carcinoma mucocullare, mucoepidermoid carcinoma, mucous carcinoma, carcinoma myxomatodes, masopharyngeal carcinoma, carcinoma *nigrum*, oat cell carcinoma, carcinoma ossificans, osteroid carcinoma, ovarian carcinoma, papillary carcinoma, periportal carcinoma, preinvasive carcinoma, prostate carcinoma, renal cell carcinoma of kidney, reserve cell carcinoma, carcinoma sarcomatodes, scheinderian carcinoma, scirrhous carcinoma, carcinoma scrota, signet-ring cell carcinoma, carcinoma simplex, small cell carcinoma, solandoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberrosum, tuberous carcinoma, verrucous carcinoma, and carcinoma vilosum.

Representative sarcomas which may be treated by the compositions of the present disclosure include, but are not limited to, liposarcomas (including myxoid liposarcomas and pleomorphic liposarcomas), leiomyosarcomas, rhabdomyosarcomas, neurofibrosarcomas, malignant peripheral nerve sheath tumors, Ewing's tumors (including Ewing's sarcoma of bone, extraskeletal or non-bone) and primitive neuroectodermal tumors (PNET), synovial sarcoma, hemangioendothelioma, fibrosarcoma, desmoids tumors, dermatofibrosarcoma protuberance (DFSP), malignant fibrous histiocytoma(MFH), hemangiopericytoma, malignant mesenchymoma, alveolar soft-part sarcoma, epithelioid sarcoma, clear cell sarcoma, desmoplastic small cell tumor, gastrointestinal stromal tumor (GIST) and osteosarcoma (also known as osteogenic sarcoma) skeletal and extraskeletal, and chondrosarcoma.

The compositions of the present disclosure may be used in the treatment of a lymphoma. Lymphomas which may be treated include mature B cell neoplasms, mature T cell and natural killer (NK) cell neoplasms, precursor lymphoid neoplasms, Hodgkin lymphomas, and immunodeficiency-associated lymphoproliferative disorders. Representative mature B cell neoplasms include, but are not limited to, B-cell chronic lymphocytic leukemia/small cell lymphoma, B-cell prolymphocytic leukemia, lymphoplasmacytic lymphoma (such as Waldenström macroglobulinemia), splenic marginal zone lymphoma, hairy cell leukemia, plasma cell neoplasms (such as plasma cell myeloma/multiple myeloma, plasmacytoma, monoclonal immunoglobulin deposition diseases, and heavy chain diseases), extranodal marginal zone B cell lymphoma (MALT lymphoma), nodal marginal zone B cell lymphoma, follicular lymphoma, primary cutaneous follicular center lymphoma, mantle cell lymphoma, diffuse large B cell lymphoma, diffuse large B-cell lymphoma associated with chronic inflammation, Epstein-Barr virus-positive DLBCL of the elderly, lymphomatoid granulomatosis, primary mediastinal (thymic) large B-cell lymphoma, intravascular large B-cell lymphoma, ALK+ large B-cell lymphoma, plasmablastic lymphoma, primary effusion lymphoma, large B-cell lymphoma arising in HHV8-associated multicentric Castleman's disease, and Burkitt lymphoma/leukemia. Representative mature T cell and NK cell neoplasms include, but are not limited to, T-cell prolymphocytic leukemia, T-cell large granular lymphocyte leukemia, aggressive NK cell leukemia, adult T-cell leukemia/lymphoma, extranodal NK/T-cell lymphoma, nasal type, enteropathy-associated T-cell lymphoma, hepatosplenic T-cell lymphoma, blastic NK cell lymphoma, lycosis fungoides/Sezary syndrome, primary cutaneous CD30-positive T cell lymphoproliferative disorders (such as primary cutaneous anaplastic large cell lymphoma and lymphomatoid papulosis), peripheral T-cell lymphoma not otherwise specified, angioimmunoblastic T cell lymphoma, and anaplastic large cell lymphoma. Representative precursor lymphoid neoplasms include B-lymphoblastic leukemia/lymphoma not otherwise specified, B-lymphoblastic leukemia/lymphoma with recurrent genetic abnormalities, or T-lymphoblastic leukemia/lymphoma. Representative Hodgkin lymphomas include classical Hodgkin lymphomas, mixed cellularity Hodgkin lymphoma, lymphocyte-rich Hodgkin lymphoma, and nodular lymphocyte-predominant Hodgkin lymphoma.

The compositions of the present disclosure may be used in the treatment of a Leukemia. Representative examples of leukemias include, but are not limited to, acute lymphoblastic leukemia (ALL), chronic lymphocytic leukemia (CLL), acute myelogenous leukemia (AML), chronic myelogenous leukemia (CML), hairy cell leukemia (HCL), T-cell prolymphocytic leukemia, adult T-cell leukemia, clonal eosinophilias, and transient myeloproliferative disease.

The compositions of the present disclosure may be used in the treatment of a germ cell tumor, for example germinomatous (such as germinoma, dysgerminoma, and seminoma), non germinomatous (such as embryonal carcinoma, endodermal sinus tumor, choriocarcinoma, teratoma, polyembryoma, and gonadoblastoma) and mixed tumors.

The compositions of the present disclosure may be used in the treatment of blastomas, for example hepatoblastoma, medulloblastoma, nephroblastoma, neuroblastoma, pancreatoblastoma, pleuropulmonary blastoma, retinoblastoma, and glioblastoma multiforme.

Representative cancers which may be treated include, but are not limited to: bone and muscle sarcomas such as chondrosarcoma, Ewing's sarcoma, malignant fibrous histiocytoma of bone/osteosarcoma, osteosarcoma, rhabdomyosarcoma, and heart cancer; brain and nervous system cancers such as astrocytoma, brainstem glioma, pilocytic astrocytoma, ependymoma, primitive neuroectodermal tumor, cerebellar astrocytoma, cerebral astrocytoma, glioma, medulloblastoma, neuroblastoma, oligodendroglioma, pineal astrocytoma, pituitary adenoma, and visual pathway and hypothalamic glioma; breast cancers including invasive lobular carcinoma, tubular carcinoma, invasive cribriform carcinoma, medullary carcinoma, male breast cancer, Phyllodes tumor, and inflammatory breast cancer; endocrine system cancers such as adrenocortical carcinoma, islet cell carcinoma, multiple endocrine neoplasia syndrome, parathyroid cancer, phemochromocytoma, thyroid cancer, and Merkel cell carcinoma; eye cancers including uveal melanoma and retinoblastoma; gastrointestinal cancers such as anal cancer, appendix cancer, cholangiocarcinoma, gastrointestinal carcinoid tumors, colon cancer, extrahepatic bile duct cancer, gallbladder cancer, gastric cancer, gastrointestinal stromal tumor, hepatocellular cancer, pancreatic cancer, and rectal cancer; genitourinary and gynecologic cancers such as bladder cancer, cervical cancer, endometrial cancer, extragonadal germ cell tumor, ovarian cancer, ovarian epithelial cancer, ovarian germ cell tumor, penile cancer, renal cell carcinoma, renal pelvis and ureter transitional cell cancer, prostate cancer, testicular cancer, gestational trophoblastic tumor, urethral cancer, uterine sarcoma, vaginal cancer, vulvar cancer, and Wilms tumor; head and neck cancers such as esophageal cancer, head and neck cancer, nasopharyngeal carcinoma, oral cancer, oropharyngeal cancer, paranasal sinus and nasal cavity cancer, pharyngeal cancer, salivary gland cancer, and hypopharyngeal cancer; hematopoietic cancers such as acute biphenotypic leukemia, acute eosinophilic leukemia, acute lymphoblastic leukemia, acute myeloid leukemia, acute myeloid dendritic cell leukemia, AIDS-related lymphoma, anaplastic large cell lymphoma, angioimmunoblastic T-cell lymphoma, B-cell prolymphocytic leukemia, Burkitt's lymphoma, chronic lymphocytic leukemia, chronic myelogenous leukemia, cutaneous T-cell lymphoma, diffuse large B-cell lymphoma, follicular lymphoma, hairy cell leukemia, hepatosplenic T-cell lymphoma, Hodgkin's lymphoma, hairy cell leukemia, intravascular large B-cell lymphoma, large granular lymphocytic leukemia, lymphoplasmacytic lymphoma, lymphomatoid granulomatosis, mantle cell lymphoma, marginal zone B-cell lymphoma, Mast cell leukemia, mediastinal large B cell lymphoma, multiple myeloma/plasma cell neoplasm, myelodysplastic syndromes, mucosa-associated lymphoid tissue lymphoma, mycosis fungoides, nodal marginal zone B cell lymphoma, non-Hodgkin lymphoma, precursor B lymphoblastic leukemia, primary central nervous system lymphoma, primary cutaneous follicular lymphoma, primary cutaneous immunocytoma, primary effusion lymphoma, plasmablastic lymphoma, Sezary syndrome, splenic marginal zone lymphoma, and T-cell prolymphocytic leukemia; skin cancers such as basal cell carcinoma, squamous cell carcinoma, skin adnexal tumors (such as sebaceous carcinoma), melanoma, Merkel cell carcinoma, sarcomas of primary cutaneous origin (such as dermatofibrosarcoma protuberans), and lymphomas of primary cutaneous origin (such as mycosis fungoides); thoracic and respiratory cancers such as bronchial adenomas/carcinoids, small cell lung cancer, mesothelioma, non-small cell lung cancer, pleuropulmonary blastoma, laryngeal cancer, and thymoma or thymic carcinoma; HIV/AIDs-related cancers such as Kaposi sarcoma; epithelioid hemangioendothelioma; desmoplastic small round cell tumor; and liposarcoma.

Methods of Administration

The therapeutic compositions as described herein can be administered by any suitable method and technique presently or prospectively known to those skilled in the art. For example, the active components described herein can be formulated in a physiologically- or pharmaceutically-acceptable form and administered by any suitable route known in the art including, for example, oral and parenteral routes of administering. As used herein, the term "parenteral" includes subcutaneous, intradermal, intravenous, intramuscular, intraperitoneal, and intrasternal administration, such as by injection. Administration of the active components of their compositions can be a single administration, or at continuous and distinct intervals as can be readily determined by a person skilled in the art.

Pharmaceutical compositions, as described herein, comprising the disclosed active components and an excipient of some sort may be useful in a variety of medical and non-medical applications. For example, pharmaceutical compositions comprising an active component described herein and an excipient may be useful for the treatment or prevention of a cancer, for example lung cancer.

"Excipients" include any and all solvents, diluents or other liquid vehicles, dispersion or suspension aids, surface active agents, isotonic agents, thickening or emulsifying agents, preservatives, solid binders, lubricants and the like, as suited to the particular dosage form desired. General considerations in formulation and/or manufacture can be found, for example, in Remington's Pharmaceutical Sciences, Sixteenth Edition, E. W. Martin (Mack Publishing Co., Easton, Pa., 1980), and Remington: The Science and Practice of Pharmacy, 21st Edition (Lippincott Williams & Wilkins, 2005).

Exemplary excipients include, but are not limited to, any non-toxic, inert solid, semisolid or liquid filler, diluent, encapsulating material or formulation auxiliary of any type. Some examples of materials which can serve as excipients include, but are not limited to, sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. As would be appreciated by one of skill in this art, the excipients may be chosen based on what the pharmaceutical composition is useful for. For example, the choice of the excipient will depend on the route of administration, the agent being delivered, time course of delivery of the agent, etc., and can be administered to humans and/or to animals, orally, rectally, parenterally, intracisternally, intravaginally, intranasally, intraperitoneally, topically (as by powders, creams, ointments, or drops), buccally, or as an oral or nasal spray. In some embodiments, the compositions disclosed herein are administered topically.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxy vinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof. Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, etc., and/or combinations thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, ascorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid. Other preservatives include tocopherol, tocopherol acetate, deteroxime mesylate, cetrimide, butylated hydroxyanisol (BHA), butylated hydroxytoluene (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary natural oils include almond, apricot kernel, avocado, babassu, bergamot, black current seed, borage, cade, chamomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *Litsea cubeba*, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Additionally, the pharmaceutical composition may further comprise a polymer. Exemplary polymers contemplated herein include, but are not limited to, cellulosic polymers and copolymers, for example, cellulose ethers such as methylcellulose (MC), hydroxyethylcellulose (HEC), hydroxypropyl cellulose (HPC), hydroxypropyl methyl cellulose (HPMC), methylhydroxyethylcellulose (MHEC), methylhydroxypropylcellulose (MHPC), carboxymethyl cellulose (CMC) and its various salts, including, e.g., the sodium salt, hydroxyethylcarboxymethylcellulose (HECMC) and its various salts, carboxymethylhydroxyethylcellulose (CMHEC) and its various salts, other polysaccharides and polysaccharide derivatives such as starch, dextran, dextran derivatives, chitosan, and alginic acid and its various salts, carageenan, various gums, including xanthan gum, guar gum, gum arabic, gum karaya, gum ghatti, konjac and gum tragacanth, glycosaminoglycans and proteoglycans such as hyaluronic acid and its salts, proteins such as gelatin, collagen, albumin, and fibrin, other polymers, for example, polyhydroxyacids such as polylactide, polyglycolide, polyl (lactide-co-glycolide) and poly(.epsilon.-caprolactone-co-glycolide)-, carboxyvinyl polymers and their salts (e.g., carbomer), polyvinylpyrrolidone (PVP), polyacrylic acid and its salts, polyacrylamide, polyacrylic acid/acrylamide copolymer, polyalkylene oxides such as polyethylene oxide, polypropylene oxide, poly(ethylene oxide-propylene oxide), and a Pluronic polymer, polyoxy ethylene (polyethylene glycol), polyanhydrides, polyvinylalchol, polyethyleneamine and polypyrridine, polyethylene glycol (PEG) polymers, such as PEGylated lipids (e.g., PEG-stearate, 1,2-Distearoyl-sn-glycero-3-Phosphoethanolamine-N-[Methoxy (Polyethylene glycol)-1000], 1,2-Distearoyl-sn-glycero-3-Phosphoethanolamine-N-[Methoxy(Polyethylene glycol)-2000], and 1,2-Distearoyl-sn-glycero-3-Phosphoethanolamine-N-[Methoxy(Polyethylene glycol)-5000]), copolymers and salts thereof.

Additionally, the pharmaceutical composition may further comprise an emulsifying agent. Exemplary emulsifying agents include, but are not limited to, a polyethylene glycol (PEG), a polypropylene glycol, a polyvinyl alcohol, a poly-N-vinyl pyrrolidone and copolymers thereof, poloxamer nonionic surfactants, neutral water-soluble polysaccharides (e.g., dextran, Ficoll, celluloses), non-cationic poly(meth) acrylates, non-cationic polyacrylates, such as poly (meth) acrylic acid, and esters amide and hydroxy alkyl amides thereof, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxy vinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof. In certain embodiments, the emulsifying agent is cholesterol.

Liquid compositions include emulsions, microemulsions, solutions, suspensions, syrups, and elixirs. In addition to the active components described herein, the liquid composition may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable compositions, for example, injectable aqueous or oleaginous suspensions may be formulated according to the known art using suitable dispersing or wetting agents and suspending agents. The sterile injectable preparation may also be an injectable solution, suspension, or emulsion in a nontoxic parenterally acceptable diluent or solvent, for example, as a solution in 1,3-butanediol. Among the acceptable vehicles and solvents for pharmaceutical or cosmetic compositions that may be employed are water, Ringer's solution, U.S.P. and isotonic sodium chloride solution. In addition, sterile, fixed oils are conventionally employed as a solvent or suspending medium. Any bland fixed oil can be employed including synthetic mono- or diglycerides. In addition, fatty acids such as oleic acid are used in the preparation of injectables. In certain embodiments, the particles are suspended in a carrier fluid comprising 1% (w/v) sodium carboxymethyl cellulose and 0.1% (v/v) Tween 80. The injectable composition can be sterilized, for example, by filtration through a bacteria-retaining filter, or by incorporating sterilizing agents in the form of sterile solid compositions which can be dissolved or dispersed in sterile water or other sterile injectable medium prior to use.

Compositions for rectal or vaginal administration may be in the form of suppositories which can be prepared by mixing the particles with suitable non-irritating excipients or carriers such as cocoa butter, polyethylene glycol, or a suppository wax which are solid at ambient temperature but liquid at body temperature and therefore melt in the rectum or vaginal cavity and release the particles.

Solid compositions include capsules, tablets, pills, powders, and granules. In such solid compositions, the solid particles are mixed with at least one excipient and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets, and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

Tablets, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. Solid compositions of a similar type may also be employed as fillers in soft and hard-filled gelatin capsules using such excipients as lactose or milk sugar as well as high molecular weight polyethylene glycols and the like.

Compositions for topical or transdermal administration include ointments, pastes, creams, lotions, gels, powders, solutions, sprays, inhalants, or patches. The active component is admixed with an excipient and any needed preservatives or buffers as may be required.

The ointments, pastes, creams, and gels may contain, in addition to the active component, excipients such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to the active component described herein, excipients such as lactose, talc, silicic acid, aluminum hydroxide, calcium silicates, and polyamide powder, or mixtures of these substances. Sprays can additionally contain customary propellants such as chlorofluorohydrocarbons.

Transdermal patches have the added advantage of providing controlled delivery of an active component to the body. Such dosage forms can be made by dissolving or dispensing the nanoparticles in a proper medium. Absorption enhancers can also be used to increase the flux of the compound across the skin. The rate can be controlled by either providing a rate controlling membrane or by dispersing the particles in a polymer matrix or gel.

In particular embodiments, the therapeutic compositions described herein may be formulated so as to be suitable for administration to the lungs. Pharmaceutical compositions for administration to the lungs can be delivery by a wide range of passive breath driven and active power driven single-/multiple-dose inhalers (DPI). The devices most commonly used for respiratory delivery include nebulizers, metered-dose inhalers, and dry powder inhalers. Several types of nebulizers are available, including jet nebulizers, ultrasonic nebulizers, and vibrating mesh nebulizers. Selection of a suitable lung delivery device depends on parameters such as the nature of the therapeutic composition and its formulation, the site of action, and the pathophysiology of the lung.

Formulations for inhalation include powder compositions, which preferably contain lactose, and spray compositions which may be formulated, for example, as aqueous solutions or suspensions or as aerosols delivery from pressurized packs, with the use of a suitable propellant, e.g., 1,1,1,2-tetrafluoroethane, 1,1,1,2,3,3,3-heptafluoropropane, carbon dioxide or other suitable gas. A class of propellants, which are believed to have minimal ozone-depleting effects in comparison to convention chlorofluorocarbons comprise hydrofluorocarbons and a number of medicinal aerosol formulations using such propellant systems have been previously described. Due to problems with the stability of pharmaceutical formulations prepared with these propellants, the addition of one or more excipients is typical, such as polar cosolvents or wetting agents (e.g., alcohols such as ethanol), alkanes, dimethyl ether, surfactants (including fluorinated and non-fluorinated surfactants, carboxylic acids such as oleic acid, polyethoxylates, etc.) or bulking agents such as a sugar and vehicles such as cromoglicic acid and/or nedocromil which are contained at concentrations that are not therapeutically and prophylactically active. For suspension aerosols, the active ingredients should be micronized so as to permit inhalation of substantially all of the active ingredients into the lungs upon administration of the aerosol formulation, thus the active ingredients will have a mean particle size of less than 100 microns, desirably less than 20 microns, and preferably in the range of 0.7 to 10 microns, for example 1 to 5 microns.

In some embodiments, the pharmaceutical composition may comprise a therapeutically effective amount of the active component described herein, a hydrofluorocarbon propellant (for example, 1,1,1,2-tetrafluoroethane, 1,1,1,2,3,3,3-heptafluoropropane, or mixtures thereof), a cosolvent (for example, ethanol), and optionally a surfactant. In some embodiments, the formulation comprises ethanol in an amount effective to disperse the active component. The propellant preferably includes a hydrofluoroalkane, in particular Propellant 134a, Propellant 227 or a mixture thereof. In the case of a mixture, the ratio of Propellant 134a to Propellant 227 is generally in a range from 75:25 w/w to 25:75 w/w. The formulations may contain a surfactant such as oleic acid, but may also be free of surfactant. The formulations are preferably free of other excipients.

The formulations may be manufactured by preparing a concentrate of the active component with ethanol and adding this concentrate to the pre-chilled propellant in a batching vessel. The resulting formulation is filled into vials. Alternatively, the formulations may be prepared by adding the required quantity of active component into an aerosol vial, crimping a valve on the vial, and introducing a premixed blend of propellant and ethanol through the valve. The vial may then be placed in an ultrasonic bath to ensure even dispersal of the active component.

In another embodiment, the pharmaceutical compositions contain the active component in particulate form, and 1,1,1,2-tetrafluoroethane, 1,1,1,2,3,3,3-hepafluoropropane, or mixtures thereof as propellant. Such formulations generally comprise from 0.01 to 5% (w/w relative to the total weight of the formulation) of polar cosolvent, in particular ethanol. In a preferred embodiment, no less than 3% w/w of polar cosolvent, in particular ethanol, is contained. Especially preferred compositions for aerosol delivery consist of particular active ingredient, and 1,1,1,2-tetrafluoroethane, 1,1,1,2,3,3,3-heptafluoropropane, or mixtures thereof as propellant and optionally a surfactant (preferably oleic acid). In the case of a mixture, the ratio of Propellant 134a to Propellant 227 is generally in a range from 75:25 w/w to 25:75 w/w.

The formulations may be prepared by adding the required quantity of active component into an aerosol vial, crimpling a valve on the vial, and introducing propellant or optionally a pre-mixed blend of propellant and optionally the cosolvent and surfactant through the valve.

Canisters generally comprise a container capable of withstanding the vapor pressure of the propellant, such as a plastic or plastic-coated glass bottle or a metal can, for example an aluminum can which may be optionally anodized, lacquer-coated and/or plastic-coated, which is closed with a metering valve. Canisters may be coated with a fluorocarbon polymer, for example, a copolymer of polyethersulfone (PES) and polytetrafluoroethylene (PTFE). Another polymer for coating that may be contemplated is fluorinated ethylene propylene (FEP).

The metering valves are designed to deliver a metered amount of the formulation per actuation and incorporate a gasket to prevent leakage of propellant through the valve. The gasket may comprise any suitable elastomeric material such as, for example, low density polyethylene, chlorobutyl, black and white butadiene-acrylonitrile rubbers, butyl rubber and neoprene. Thermoplastic elastomer valves and valves containing EPDM rubber may be suitable. Suitable valves are commercially available from manufacturers well known in the aerosol industry.

Valve seals, especially the gasket seal and also the seals around the metering chamber, can be manufactured of a material which is inert to and resists extraction into the contents of the formulation, especially when the contents include a cosolvent such as ethanol.

Valve materials, especially the material of manufacture of the metering chamber, can be manufactured of a material which is inert to and resists distorting by contents of the formulation, especially when the contents include a cosolvent such as ethanol. Particularly suitable materials for use in manufacture of the metering chamber include polyesters e.g. polybutyleneterephthalate and acetals.

Materials of manufacture of the metering chamber and/or the valve stem may desirably be fluorinated, partially fluorinated, or impregnated with fluorine containing substances in order to resists drug deposition.

Valves, which are entirely or substantially composed of metal components are especially preferred.

Intranasal sprays or nasal drops may be formulated with aqueous or non-aqueous vehicles with or without the addition of agents such as thickening agents, buffer salts or acid or base to adjust the pH, isotonicity adjusting agents, preservatives, or anti-oxidants.

Formulations for inhalation by nebulization may be formulated with an aqueous vehicle with the addition of agents such as acid or base, buffer salts, isotonicity adjusting agents or antimicrobials. They may be sterilized by filtration or heating in an autoclave. Suitable technologies for this type of administration are known in the art.

The active ingredient may be administered in such amounts, time, and route deemed necessary in order to achieve the desired result. The exact amount of the active ingredient will vary from subject to subject, depending on the species, age, and general condition of the subject, the severity of the infection, the particular active ingredient, its mode of administration, its mode of activity, and the like. The active ingredient, whether the active compound itself, or the active compound in combination with an agent, is preferably formulated in dosage unit form for ease of administration and uniformity of dosage. It will be understood, however, that the total daily usage of the active ingredient will be decided by the attending physician within the scope of sound medical judgment. The specific therapeutically effective dose level for any particular subject will depend upon a variety of factors including the disorder being treated and the severity of the disorder; the activity of the active ingredient employed; the specific composition employed; the age, body weight, general health, sex and diet of the patient; the time of administration, route of administration, and rate of excretion of the specific active ingredient employed; the duration of the treatment; drugs used in combination or coincidental with the specific active ingredient employed; and like factors well known in the medical arts.

The active ingredient may be administered by any route. In some embodiments, the active ingredient is administered via a variety of routes, including oral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, enteral, sublingual; by intratracheal instillation, bronchial instillation, and/or inhalation; and/or as an oral spray, nasal spray, and/or aerosol. In general, the most appropriate route of administration will depend upon a variety of factors including the nature of the active ingredient (e.g., its stability in the environment of the gastrointestinal tract), the condition of the subject (e.g., whether the subject is able to tolerate oral administration), etc.

The exact amount of an active ingredient required to achieve a therapeutically or prophylactically effective amount will vary from subject to subject, depending on species, age, and general condition of a subject, severity of the side effects or disorder, identity of the particular compound(s), mode of administration, and the like. The amount to be administered to, for example, a child or an adolescent can be determined by a medical practitioner or person skilled in the art and can be lower or the same as that administered to an adult.

Useful dosages of the active agents and pharmaceutical compositions disclosed herein can be determined by comparing their in vitro activity, and in vivo activity in animal models. Methods for the extrapolation of effective dosages in mice, and other animals, to humans are known to the art.

The dosage ranges for the administration of the compositions are those large enough to produce the desired effect in which the symptoms or disorder are affected. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counterindications. Dosage can vary, and can be administered in one or more dose administrations daily, for one or several days.

The therapeutic compositions described herein may be administered independently or in combination with other anti-cancer therapies, including surgery, radiation therapy, chemotherapy, DNA therapy, adjuvant therapy, gene therapy, and additional therapeutic agents for the treatment of cancer. Additional therapeutic agents may be alkylating agents, angiogenesis inhibitors, antibodies, antimetabolites, antimitotics, antiproliferatives, aurora kinase inhibitors, Bcl-2 family protein (for example, Bcl-xL, Bcl-2, Bcl-W) inhibitors, Bcr-Abl kinase inhibitors, biologic response modifies, cyclin-dependent kinase inhibitors, cell cycle inhibitors, cyclooxygenase-2 inhibitors, leukemia viral oncogene homolog (ErbB2) receptor inhibitors, growth factor inhibitors, heat shock protein (HSP)-90 inhibitors, histone deacetylase (HDAC) inhibitors, hormonal therapies, inhibitors of apoptosis proteins (IAPs), immunological agents, intercalating antibiotics, kinase inhibitors, mammalian target of rapamycin inhibitors, mitogen-activated extracellular signal-regulated kinase inhibitors, microRNAs, small inhibitory ribonucleic acid (siRNAs), non-steroidal anti-inflammatory drugs (NSAIDs), poly ADP (adenosine diphosphate)-ribose polymerase (PARP) inhibitors, platinum chemotherapeutics, polo-like kinase inhibitors, proteasome inhibitors, purine analogs, pyrimidine analogs, receptor tyrosine kinase inhibitors, retinoids/deltoids, plant alkaloids, topoisomerase inhibitors, and the like.

A number of embodiments of the disclosure have been described. Nevertheless, it will be understood that various modifications may be made without departing from the spirit and scope of the invention. Accordingly, other embodiments are within the scope of the following claims.

By way of non-limiting illustration, examples of certain embodiments of the present disclosure are given below.

EXAMPLES

The following examples are put forth so as to provide those of ordinary skill in the art with a complete disclosure and description of how the compositions and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in degrees Celsius or is at ambient temperature, and pressure is at or near atmospheric.

Figure 1A:
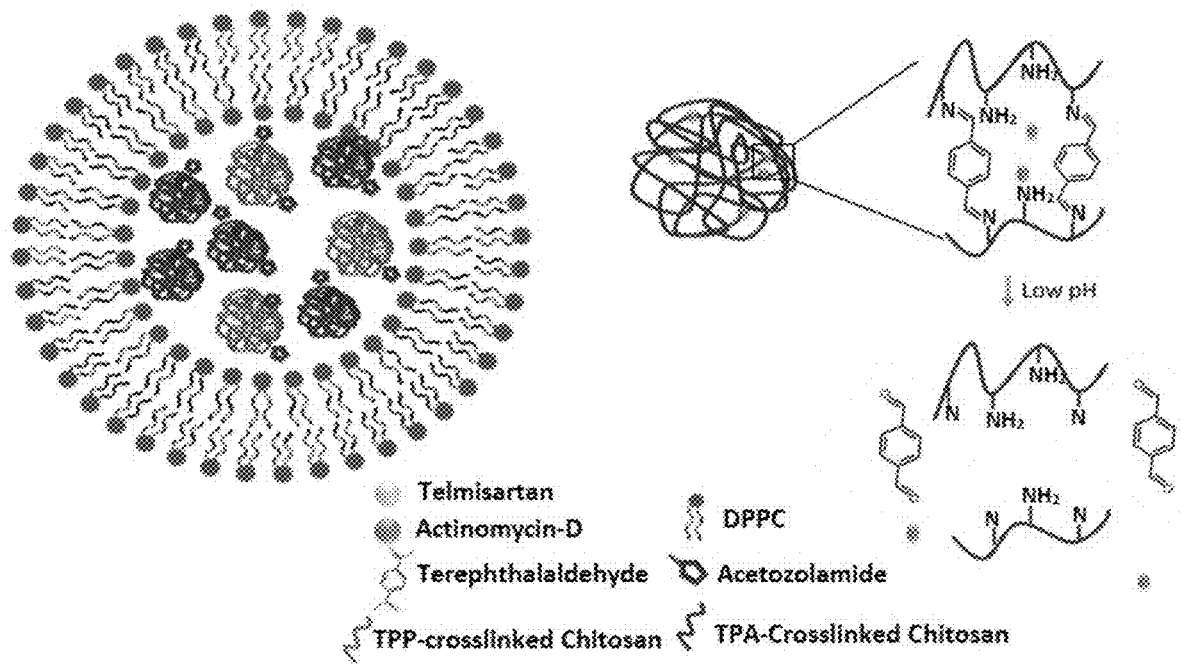

Example 1. Microparticles for Controlled Release of Telmisartan and Actinomycin D Combination for Lung Cancer Therapy In this example, a novel drug delivery system for lung cancer therapy is developed which is able not only to protect the drugs from degradation but also to deliver them at intended sites and minimize the side effects. Chitosan-based nanoparticles have been extensively used to deliver anticancer drugs and can be administered through various routes including intranasal. Herein, a novel particle is described consisting of lipids and chitosan polymers that would be able to deliver drugs directly to the lungs and release its payload in a targeted and controlled way. A schematic representation of the proposed drug delivery system is seen in FIG. 1. The core of the nanoparticle is composed of two different types of chitosan nanoparticles loaded either with Telmisartan or ActD. The Act-D-chitosan nanoparticle is designed for controlled release of its payload. For this reason, pH responsive nanoparticles, using terephthalaldehyde (TPA) crosslinked chitosan are used. In a neutral pH the NPs are stable but in an acidic environment crosslinked chitosan are decomposed for fast and controlled release of the drugs. Telmisartan is entrapped on regular tripolyphosphate (TPP)-crosslinked chitosan NPs for sustained release. Both types of Chitosan NPs will be loaded on liposomal microparticles.

Figure 1B:
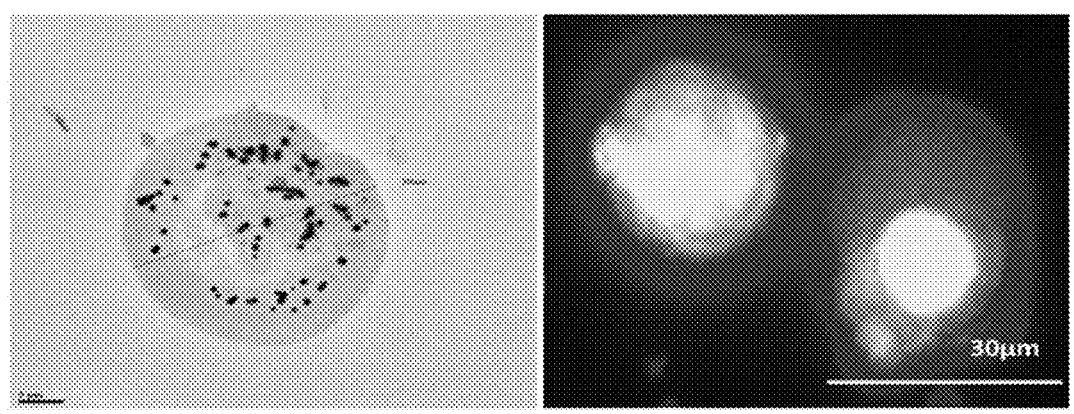

Furthermore, acetazolamide, which is a hypoxia-targeting moiety, is conjugated on the surface of both types of nanoparticles. This targeting moiety ensures the accumulation of the nanoparticles deep in the tumor core and will ensure the effectiveness of this delivery approach. The size and morphology of the nanoparticles was confirmed using TEM and fluorescent microscopy. As seen in FIG. 1B, the diameter of the microparticle is 30 μm and nanoparticles are successfully loaded onto the microparticles. The successfully loading of the nanoparticles onto microparticles was further confirmed using fluorescent microscopy. As seen in FIG. 1B there is a strong FITC-nanoparticle signal on the core of the rhodamine-labelled microparticles indicating the successful nanoparticle loading to microparticles.

Development of a Deep Lung Delivery System

Figure 2A:
Figure 2B:
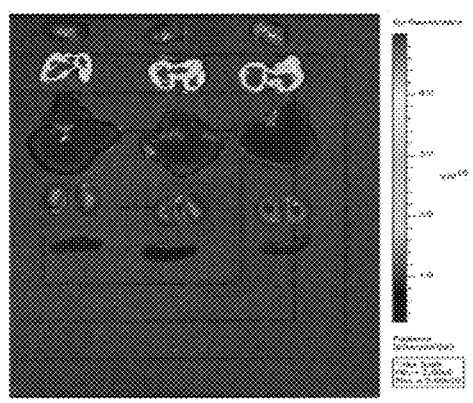
Figure 2C:
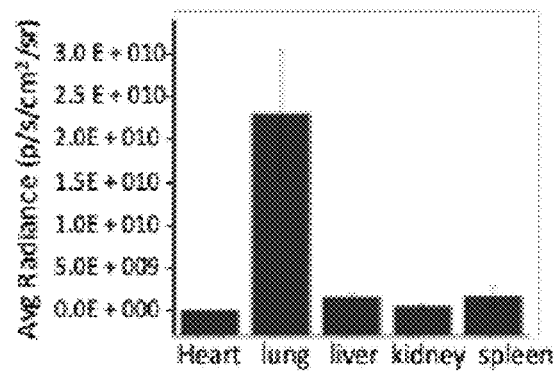
Figure 2D:
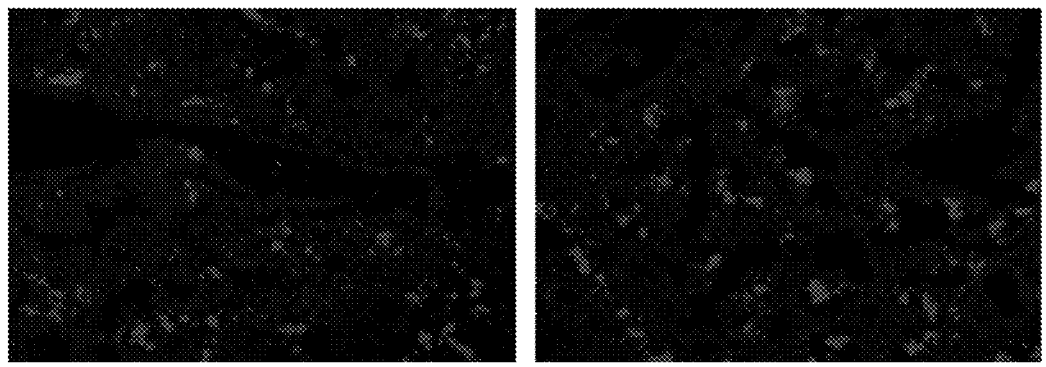
Figure 2E:
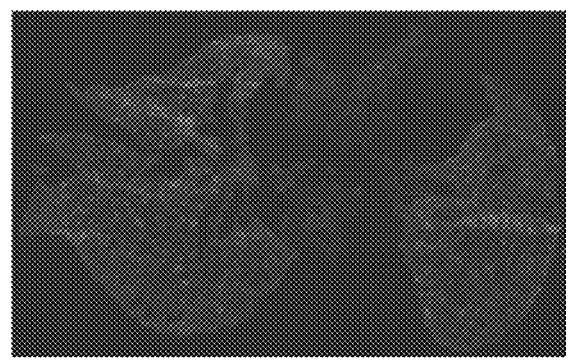

A 'Nano-Cell' strategy was previously successfully used that used 30-50 μm large SCs packaged with NPs, to deliver Doxorubicin to deep lung. Since cell-packaged NP create translational complexities, it was tested whether the cells can be replaced with 30 μm liposomal particles (FIG. 2A) and achieve the same result. It was found that lipid (DPPC)-based microparticles (ML) with size of 30 μm given intravenously (i.v.) go to the lung (FIG. 2B-C) as assessed by IVIS and specifically to the deep lung. Microscopic analyses of lung sections after 30 min of i.v. delivery into mice showed that the MLs go to the deep lung (FIG. 2D-E).

Synthesis of Chitosan Nanoparticles with pH-Inducible Drug Release

Figure 3A:
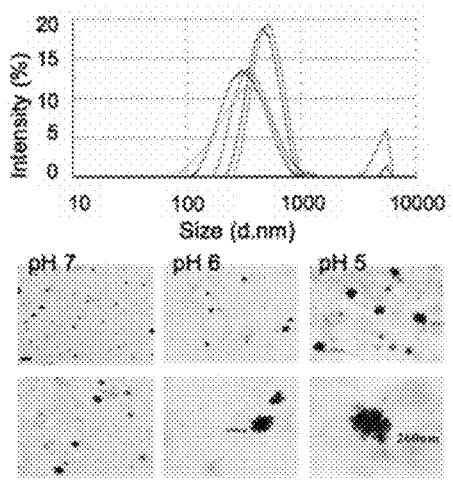
Figure 3B:
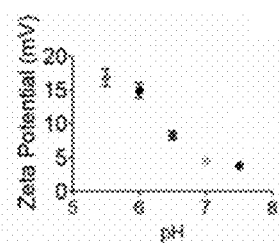
Figure 3C:
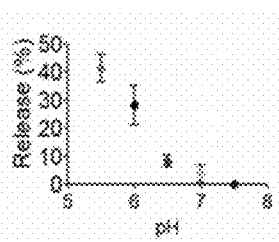
Figure 3D:
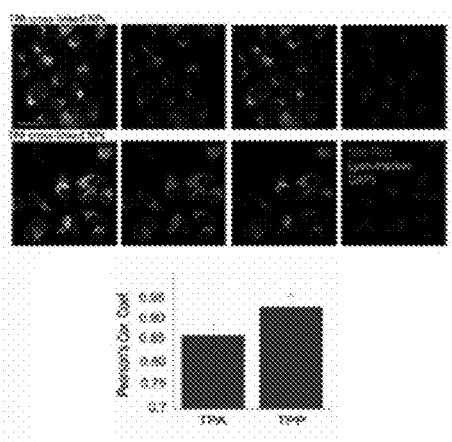

To devise a differential release of hydrophobic and hydrophilic drugs, chitosan NPs were synthesized, which are classified as GRAS (generally regarded as safe) by FDA, using simple self-assembly synthesis and cell-targeted delivery. The effect of the pH on terephthalaldehyde (TPA)-crosslinked chitosan NPs was examined, and the size (FIG. 3A) and zeta potential (FIG. 3B) was tested using dynamic laser scattering (DLS). To investigate the effect of lower pH on its size and zeta potential, Nile Red encapsulated TPA-Crosslinked chitosan particles were incubated in different pH in the range from 7.4 to 5.5. The size of particles was found to increase drastically in pH 6 due to chitosan protonation and TPA removal (FIG. 3A) while the zeta potential increases from 3.64 mV to 16 mV. To further investigate the effect of pH on the release, Nile Red (FIG. 3C-D) encapsulated TPA-Crosslinked chitosan particles were incubated in different pH in the range for 30 minutes and then transferred to pH 7.4 medium. These results revealed that 30% of the encapsulated dyes were released in pH 6.0 confirming the fast release and the pH responsive properties of these NPs. Further, Nile red showed strong fluorescence enhancement upon transition from aqueous to hydrophobic environments. In an acidic environment (such as lysosomes), TPA cross-linked NPs released Nile red and the fluorescence intensity of Nile red in lysosomes was lower compared to TPP crosslinked NPs.

Synthesis of Chitosan Nanoparticles for Sustained Release of Payload

TPP-crosslinked chitosan nanoparticles loaded with Telmisartan were also prepared. These particles are designed for sustained release of their payload. The size, morphology and zeta potential were tested using transmission electron microscopy and dynamic laser scattering (FIGS. 4A&B and C). Telmisartan release from the TPP-chitosan particles was also tested (FIG. 4D). It was found that TPP-crosslinked particles have a final size of 150 nm with a positive final zeta potential and they release 100% of their payload within 70 hours.

It will be apparent to those skilled in the art that various modification and variations can be made in the present disclosure without departing from the scope or spirit of the disclosure. Other embodiments of the disclosure will be apparent to those skilled in the art from consideration of the specification and practice of the disclosure herein. It is intended that the specification and examples be considered as exemplary only, with a true scope and spirit of the disclosure being indicated by the following claims.

What is claimed is:

1. A therapeutic composition comprising:
   a plurality of liposomal microparticles;
   a plurality of terephthalaldehyde (TPA)-crosslinked chitosan nanoparticles encapsulated within the liposomal microparticles, wherein the TPA-crosslinked chitosan nanoparticles are loaded with actinomycin D; and
   a plurality of tripolyphosphate (TPP)-crosslinked chitosan nanoparticles encapsulated within the liposomal microparticles, wherein the TPP-crosslinked chitosan nanoparticles are loaded with telmisartan.

2. The therapeutic composition of claim 1, wherein the liposomal microparticles have an average particle diameter ranging from about 25 to about 55 microns.

3. The therapeutic composition of claim 1, wherein the liposomal microparticles comprise dipalmitoylphosphatidylcholine (DPPC).

4. The therapeutic composition of claim 1, wherein the TPA-crosslinked chitosan nanoparticles have an average particle diameter ranging from about 300 nm to about 700 nm at a pH of greater than about 7.

5. The therapeutic composition of claim 1, wherein the TPA-crosslinked chitosan nanoparticles have a zeta potential ranging from about 2 mV to about 5 mV at a pH of greater than about 7.

6. The therapeutic composition of claim 1, wherein the TPA-crosslinked chitosan nanoparticles release actinomycin D at a pH of less than about 7.

7. The therapeutic composition of claim 6, wherein the average particle diameter of the TPA-crosslinked chitosan nanoparticles increases by an amount ranging from about 100 nm to about 300 nm at a pH of less than about 7.

8. The therapeutic composition of claim 6, wherein the zeta potential of the TPA-crosslinked chitosan nanoparticles increases by an amount ranging from about 5 mV to about 15 mV at a pH of less than about 7.

9. The therapeutic composition of claim 6, wherein the TPA-crosslinked chitosan nanoparticles release at least 25% of the loaded actinomycin D within 30 minutes at a pH of less than about 7.

10. The therapeutic composition of claim 1, wherein the therapeutic composition further comprises acetazolamide, wherein acetazolamide is conjugated to a surface of the TPA-crosslinked chitosan nanoparticles.

11. The therapeutic composition of claim 1, wherein the TPP-crosslinked chitosan nanoparticles have an average particle diameter from about 50 nm to about 500 nm.

12. The therapeutic composition of claim 1, wherein the TPP-crosslinked chitosan nanoparticles have a zeta potential ranging from about 5 mV to about 50 mV.

13. The therapeutic composition of claim 1, wherein the TPP-crosslinked chitosan nanoparticles provide sustained release of telmisartan.

14. The therapeutic composition of claim 1, wherein the therapeutic composition further comprises acetazolamide, wherein acetazolamide is conjugated to a surface of the TPP-crosslinked chitosan nanoparticles.

15. The therapeutic composition of claim 1, further comprising one or more additional therapeutic agents.

16. The therapeutic composition of claim 1 formulated for delivery to the lung.

17. A method of treating lung cancer in a subject comprising administering a therapeutically effective amount of the composition of claim 1 to the subject.

18. The method of claim 17, wherein the composition is administered to the lung.

* * * * *